United States Patent [19]

Vairel et al.

[11] 4,029,767

[45] June 14, 1977

[54] PHARMACEUTICAL COMPOSITIONS OF STABLE UROKINASE-HEPARIN COMPLEXES AND METHODS FOR USE THEREOF

[75] Inventors: Edmond G. Vairel, Paris; Jean Goulay, Oissel; Jean Choay, Paris, all of France

[73] Assignee: Choay S.A., Paris, France

[22] Filed: Nov. 5, 1975

[21] Appl. No.: 629,076

Related U.S. Application Data

[62] Division of Ser. No. 292,139, Sept. 25, 1972, Pat. No. 3,926,727.

[30] Foreign Application Priority Data

Sept. 24, 1971 France .............................. 71.34435
June 30, 1972 France .............................. 72.23867
June 30, 1972 France .............................. 72.23868

[52] U.S. Cl. .................................. 424/94; 424/183
[51] Int. Cl.² ................ A61K 37/48; A61K 31/725
[58] Field of Search .............................. 424/94, 183

[56] References Cited

UNITED STATES PATENTS 3,726,969  4/1973  Johnson et al. ..................... 424/94

*Primary Examiner*—Sam Rosen
*Attorney, Agent, or Firm*—Weiser, Stapler & Spivak

[57] ABSTRACT

The present invention relates to pharmaceutical compositions of stable urokinase-heparin complexes, wherein the urokinase is purified, and methods for use thereof.

20 Claims, 1 Drawing Figure

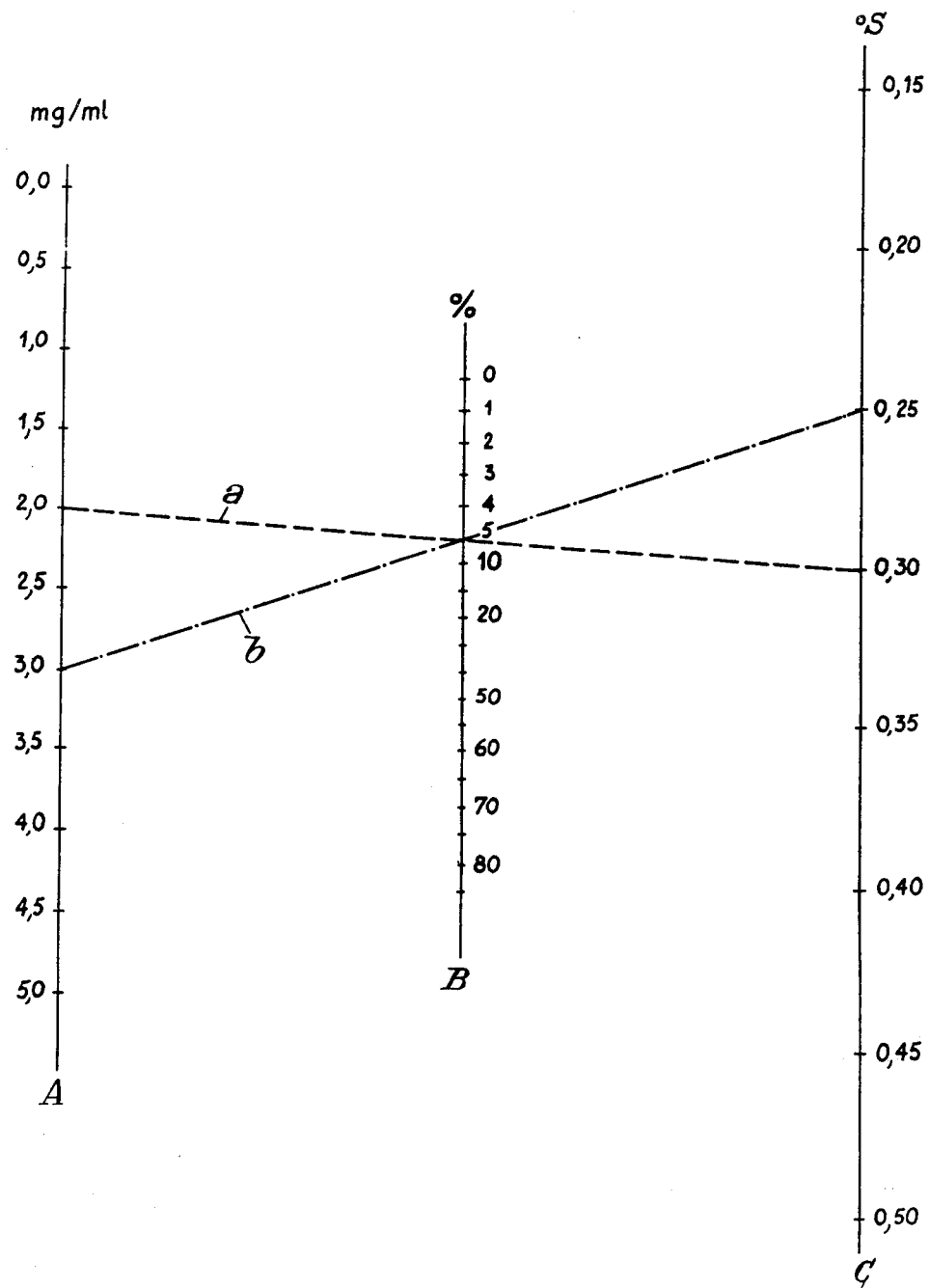

PHARMACEUTICAL COMPOSITIONS OF STABLE UROKINASE-HEPARIN COMPLEXES AND METHODS FOR USE THEREOF

This application is a division of prior U.S. Application No. 292,139 filed Sept. 25, 1972, now issued as U.S. Pat. No. 3,926,727.

The invention relates to a method for the preparation and for the purification, of biologically active substances and it relates more particularly, because it is in this case that its application seems to offer most advantage, but not exclusively, to a method for the preparation and for the purification of urokinases contained in biological media, especially from urine of animal origin or, more particularly again, of human origin.

It relates also to a method of depyrogenation (that is to say the elimination of pyrogenic substances) from these biologically active substances, more particularly from urokinase.

Finally it relates to a method for the stabilisation of biological substances, especially of the urokinase, to the products, more particularly to the complexes of urokinase which can be obtained, especially by the application of this method, as well as to the compositions and medicaments into which enter the complexes of the type concerned.

It is known that urokinase is an enzyme present in urine and which catalyses the transformation of the plasminogen into plasmin, of which peptidase the physiological role is to dissolve intravascular fibrinous formations. A fault in the mechanisms of activation of the plasminogen, in the case of accelerated kinetics of the coagulating system or of alteration of the vascular walls, lead to the maintenance of intravascular fibrin which in the end provokes various thrombo-embolic syndromes (thrombosis, embolisms, disseminated intravascular coagulation, etc.). The administration of urokinase in these pathological cases causes acceleration of the formation of plasmin, especially at the level of fibrinous formations, as indicated in the literature.

Urokinase therefore constitutes the preferred treatment of thrombo-embolic syndromes and its human origin avoids the dangers of anaphylactic shock.

There have already been proposed a certain number of methods for obtaining purified preparations of urokinase, which methods however involve, generally, relatively high losses in yield of urokinase. These losses in yield can hence be all the more desirable as the production costs of purified urokinase are higher and, in the case of urokinase extracted from human urine, as the collection of the latter in large amounts is difficult.

In addition known purification methods do not generally allow the production of urokinase preparations whose content of pyrogenic substances is sufficiently reduced for their use in therapeutics to be easy. In fact this content of pyrogenic substances is of such a nature as to constitute a drawback which can become serious if account is taken of the extreme sensitivity often observed to arise in patients from treatment based on urokinase, which treatment involes the administration by the intravenous route of doses of the urokinase which can be high, capable, for example, of reaching 150,000 CTA units or more in a single injection.

Another difficulty finally resides in the problem of obtaining urokinase preparations of high stability, which complicates storage problems as well as those relating to the administration of these preparations to patients.

It will be noted in particular that this administration, which is generally carried out by the continuous venous perfusion of preparations of urokinase diluted in, particularly, glucose serum, is rendered delicate by the fact of the instability of the enzyme in dilute solution, which obliges very frequent renewal of the solution or proceding by discontinuous injections of a concentrated solution of urokinase into the tubing of a perfusion of glucose serum, when this perfusion is placed in position. Standard units of urokinase activity adopted by the Commitee on Thrombolytic Agents, National Heart Institute, U.S.A.

It is an object of the invention to overcome these drawbacks.

It is a particular object of the invention to provide a method for the preparation and/or purification which enables the production of concentrated urokinase preparations containing practically the whole of the urokinase activity of the initial medium to which the method of the type concerned is applied.

Another object of the invention is to provide a method which enables the separation from biologically active substances, especially from urokinase, of the pyrogenic substances which accompany them, at least to a sufficient degree for the biologically active substances concerned to be practically a pyrogenic at high doses.

Yet another object of the invention is to provide a preparation stablised in urokinase activity, which is easily storable and whose administration to patients can be effected by simple perfusion of a solution of this preparation and this during several hours.

In one embodiment of the method according to the invention for obtaining a preparation enriched in urokinase from a concentrated solution of crude urokinase, obtained in a manner known in itself, especially from human urine, the method comprises one or other of the following steps, the second preferably following immediately after the first:

the first step comprising exclusion chromatography by placing the above-said concentrated solution of crude urokinase in contact with a diethylaminoethyl-cellulose resin, known under the connotation DEAE cellulose, this first step being characterised in that the conductivity of the above-said solution is previously adjusted to a value comprised between about 15,000 and about 25,000 micromhos and its pH to a value comprised between about 4 and about 6, preferably equal to 4.5, and that the effluent is collected and, preferably, that the resin is washed with a solution of ammonium sulphate at pH 4.5 and of which the conductivity is of the order of 15,000 micromhos;

the second step, which is preferably carried out on an initial solution resulting from the combination of the effluent and the washings obtained at the outlet from the above-said first step, comprising a second exclusion chromatography by placing this solution in contact with a diethylaminocellulose resin, this second step being characterised in that, prior to this placing in contact, on the one hand, the conductivity of the solution is adjusted to a value at least equal to 15,000 micromhos, preferably comprised between 15,000 and 18,000 micromhos, and its pH to a value comprised between 6 and 7, preferably comprised between 6.6 and 6.8 and, on the other hand, the weight of resin used in this second exclusion chromatography is adjusted with relation to the urokinase activity of the solution to a sufficiently high value for it to be possible to observe a retention of proteins on the resin under the above-indicated conditions of conductivity and of pH, this value not however exceeding that for which there would also be observed a non-negligible retention of urokinase on the resin; and, finally, as regards the conductivity of the solution in contact with the resin is, during the above-said second exclusion chromatography, brought by successive steps, by addition of apyrogenic distilled water, to a final value of the order of 9,000 micromhos.

Advantageously, each addition of water is such that it produces the lowering of conductivity of the medium by a value of the order of 1,000 micromhos, each addition being separated by a shaking operating during a time comprised between 5 and 15 minutes, preferably of the order of 10 minutes.

All the preceding operations are, preferably, effected at a temperature of the order of 4° C.

It will be observed that the invention has thus proposed conditions in which preferential absorption of the proteinic impurities contained in the concentrated solution of urokinase occurs, the latter not itself being retained on the resin. The principal parameter playing part in the establishment of these differential absorption conditions, is constituted by the conductivity of the treated solutions.

Respect for the ranges of conductivity, under the pH conditions indicated above, is essential for the good operation of the method according to the invention and for the obtaining of high yields of urokinase. It will be noted in particular that, in the case of the first exclusion chromatography, the resin can fix neither urokinase, nor proteinic impurities if the initial conductivity of the concentrated solution of urokinase is higher than 25,000 micromhos. It absorbs on the other hand at the same time urokinase and the proteinic impurities if the conductivity of the concentrated solution of urokinase is adjusted to a value below 10,000 micromhos.

It is the same at the stage of the second exclusion chromatography. For initial conductivities of 15,000 to 18,000 micromhos of the treated solution there is observed a very selective absorption of the proteins. Each of the successive dilutions results in an additional absorption of proteins on the resin. The gradual saturation of the latter involves a reduction in its affinity for urokinase, so that the above-said successive dilutions can be pursued to a value of 9,000 micromhos, without risk of also absorbing urokinase resulting therefrom.

Similarly it is important, especially in the second exclusion chromatography to keep the values of the ratio of the amount of resin applied to the urokinase activity of the treated solution between certain limits.

This ratio can vary within rather wide limits in the first exclusion chromatography. It has been observed in particular that similar results are obtained for all values of this ratio comprised between about 15g and 40g of dry resin per 14 million CTA units of urokinase.

The selection of this ratio is more critical in the case of the second exclusion chromatography. It must be kept, especially for the values of the conductivity located around 22,000 micromhos, between about 30 and about 60g of dry resin per 10 million CTA units of urokinase of the solution to be treated, the best results being obtained for values comprised between 40 and 53g of dry resin per 10 million CTA units of urokinase.

In certain cases the concentrated solution of urokinase can be subjected directly to the above-said second exclusion chromatography, especially in the case where recourse is had, in the steps of final purification, to special subsequent steps of separation of the pyrogenic substances which, in human urine, always accompany the urokinase. In practice it is however mostly preferable to start with the above-said first exclusion chromatography. The latter enables in fact, besides a first elimination of a small amount of protein impurities, the obtaining of a perfectly clear solution and a first depyrogenation of the urokinase.

The method according to the invention enables a considerable enrichment of the urokinase relative to the proteins which initially accompany it, 50 to 60% of the proteins being removed, with a total yield of urokinase activity. It is especially noted that the solution obtained at the end of the first exclusion chromatography contains the same number of units of urokinase as the initial solution. The number of units of urokinase collected at the end of the second exclusion chromatography is even slightly greater than that of the solution subjected to the second exclusion chromatography, which can possibly be interpreted by the absorption on the resin of a urokinase inhibitor. The total yield in urokinase activity constitutes therefore a distinct advantage of the method according to the invention, especially if account is taken of the difficulties that are encountered in collecting human urine in large quantities, on the one hand, and the considerable expense of production of purified urokinase, on the other hand.

The solution thus enriched in urokinase can again be further purified by having recourse to additional treatments known in principle, especially by absorption of the solution on kaolin, then by absorption chromatography on resin of the Amberlite type or again by absorption chromatography on carboxymethylcellulose.

The method according to the invention, completed by one of the techniques which have been described and applied to a solution of crude urokinase extracted from human urine finally enables the removal of 80–90% of the proteins which initially accompany the urokinase, without notable losses of urokinase activity.

The concentrated solution of crude urokinase initially applied can be obtained in any manner known in itself, for example in the case of the extraction of urokinase from very dilute solutions, such as urine, especially human urine, by placing the latter in contact with an absorption agent for the proteins and by elution of the absorbate. There are described in the literature various methods enabling the production of initial concentrated solutions of crude urokinase, these methods utilising absorption agents as diverse as, for example, silicate gel, cation exchange silicates, salts such as barium sulphate, resins such as oxycellulose, etc.

Advantageously, recourse will be had to the placing of the solutions in contact with a filtration adjuvant such as that marketed under the trademark "Hyflosupercel," this operation being followed by re-extraction of the urokinase and of the proteins absorbed by the filtration adjuvant, by a salting out of the urokinase contained in the extraction solution by means of ammonium sulphate, by solution of the precipitate obtained in a glucose solution and by dialysis of the latter to obtain finally a dialysate which is subjected to one of the exclusion chromatagraphy steps, preferably the first, of the method according to the invention.

The method according to the invention hence enables the obtaining of concentrated preparations of urokinase having already a high degree of purity and a reduced content of pyregenic substances, these preparations already lending themselves very effectively to human clinical treatment. This content of pyrogenic substances is not however yet negligible. In fact purified preparations of urokinase obtained by the method according to the invention still produce a certain hyperthermia in the rabbit when the doses administered exceed a moderately high threshold. Injected in rabbits under the conditions according to the general methods of analysis of the French Pharmacopea, 8th edition, page 1615, at the dose of 3,000 CTA units/kg, these purified preparations of urokinase produce an elevation of temperature which varies from 0.5° to 0.9° C from one rabbit to the other.

In order to obtain preparations of urokinase having still fuerther reduced contents of pyrogenic substances recourse is had to the method according to the invention of purification, more particularly of depyrogenation, from proteinic substances with biological activity, especially urokinase, which preferably are subjected to a first purification, this method being characterised in that a partial saturation of this solution is produced with an agent for the precipitation of the proteins to a degree, which is a function of the initial concentration in the solution of the proteins, such that this partial saturation only induces the precipitation of a portion of the proteins contained in the initial solution, this portion being sufficiently reduced for its content in the proteinic substance with biological activity to be maintained in predetermined low proportions, if not practically negligible, and the supernatant liquid is collected.

In a preferred embodiment of the method according to the invention, applied to urokinase, the precipitating agent is constituted by ammonium sulphate, the abovesaid partial precipitation being effected on a urokinase solution containing from 1.5 to 3 mg of proteins per ml, at a pH comprised between 3 an 4.5, preferably of the order of 3.8, the conductivity of this solution having been adjusted previously to a value comprised between 15,000 and 25,000 micromhos, the degree of saturation of the solution in ammonium sulphate, comprised between 0.25 to 0.35, not being pushed beyond that which produces precipitation of proteins containing more than 5% of the urokinase activity contained in the initial solution (being understood that the degree of saturation of a solution equals 1, when the solution if completely saturated: that is to say by the solution of 700 g of ammonium sulphate in 1,000 ml of distilled water at +4° C). The urokinase practically free of pyrogenic substances contained in the supernatant liquid can then be isolated, especially by salting the solution with crystalline ammonium sulphate.

It will be appreciated that, taking into account the preferred ranges of concentrations of proteins indicated above, it will be advantageous to proceed with a preliminary purification as extensive as possible of the urokinases to be treated, to eliminate the maximum possible of proteins, so that it is not necessary to operate with too large volumes of solution. In other words, the method according to the invention constitutes, in one of its preferred applications a final purification step intended to perfect the effects of a preliminary purification method.

Advantageously recourse will be had to the method of purification according to the invention described above, comprising the two above-indicated exclusion chromatography steps, completed by a third step comprising:

either an absorption chromatography on carboxymethylcellulose of the urokinase contained in the solution resulting from combination of the effluent and the washings from the resin of the second exclusion chromatography, at a pH of the order 5, and the elution of the urokinase absorbed on carboxymethylcellulose with a phosphate buffer at pH 6.8 – 6.9, or an absorption of the solution resulting from the combination of the effluent and the washings of the second exclusion chromatography on kaolin at pH 6.2, the elution of the urokinase held on the kaolin by a solution of ammonium chloride in 4% ammonia, precipitation with ammonium sulphate, taking up the precipitate in water and dialysis of the suspension against an 0.05 M phosphate solution buffered to pH 6.2, filtration of the dialysate on a column of resin of the Amberlite IRC 50 type, and elution of the resin to recover the urokinase.

It has been noted, as already indicated above, that the degree of saturation of the solution in the ammonium sulphate which produces the formation of a precipitated protein, (among which are the pyrogenic substances) retaining a given minimum percentage of urokinase varies as a function, especially inversely, of the initial content of proteins of the treated solution.

The values which are suitable to be given to this degree of saturation, taking into account the initial content of the solution in proteins, will be apparent especially from the graph of the single FIGURE of the accompanying drawings. These values have been determined experimentally, especially on solutions purified according to the preferred method of purification indicated below, in particular on those obtained in the Examples described below. The axis A of the single FIGURE is graduated in concentrations of proteins (in mg/ml) of solutions to be treated, the C axis in degrees of saturation (°S) of the solution of ammonium sulphate and the B axis in percent of urokinase entrained in the precipitated proteins formed under the conditions of the invention. The relative arrangements of these axes and the scales of their graduations have been selected so that the percentage of urokinase entrained is, in each case, given by the point of intersection with the B axis of a line passing through the points representing the concentration in proteins, on the A axis, and of the degree of saturation in ammonium sulphate on the C axis respectively. Thus there is obtained, for example, a protein precipitate holding 5% of the urokinase activity of the initial solution, by bringing to 0.30 the degree of saturation in ammonium sulphate of the solution, when the initial content in proteins of the latter is 2 mg/ml (dashed line $a$), or by bringing it to 0.25 when this initial content is 3 mg/ml (mixed line $b$).

Considering for example, the case of an initial solution of urokinase containing 2mg/ml of proteins, in more specific manner, the following observations may be made.

Up to a value of the degree of saturation equal to 0.20, there is no formation of precipitate. The solution obtained hence conserves its pyrogenic substances. At the same concentration of proteins and with a degree of saturation equal to 0.25, a slight precipitate begins to be formed, this precipitate retaining about 2.5% of the urokinase contained in the medium. This saturation is not sufficient to retain the whole of the pyrogenic substances. On the other hand, with a degree of saturation of 0.30, the precipitate formed which contains about 5% of urokinase, retains also the larger part of the pyrogenic substances. The supernatant liquid, which still contains 95% of the total urokinase activity contained in the initial solution, if free of pyrogenic substances according to the standards fixed by the French Pharmacopea already mentioned, at doses as high as 15,000 CTA units/kg. At a saturation above 0.30, the supernatant liquid will also be a pyrogenic at the same doses but the amount of urokinase retained on the precipitate will be greater, as shown in the graph.

The invention relates lastly to a method of stabilising urokinase, which method consists of causing a purified solution of urokinase to react with a solution of heparin; preferably in acidified medium, at a pH comprised between 1 and 5, preferably 4.2, and in collecting the precipitate formed, particularly by centrifugation.

Advantageously the initial solution of purified urokinase is obtained by the application of the enrichment method described above, if necessary completed by the depyrogenation method also described above.

The invention also relates to the product obtained by the reaction of the solution of urokinase with a solution of heparin, which product is constituted by a complex of urokinase and heparin, which complex, will be called below "urokinase heparinate," it being understood that the expression urokinase covers both pure urokinase and so-called purified urokinases, used until now in therapeutics.

Urokinase heparinate is a complex occurring in the form of aggregates and whose molecular weight is a function of that of the heparin used and of the original proteinic impurities accompanying, as the case may be, the urokinase. In this complex the activity of heparin is negligible in respect to that of the urokinase. In fact, the heparin due to its numerous acid functional groups, can fix numerous molecules of urokinase.

Urokinase heparinate is soluble at pH 7 and precipitates when the solutionis acidified to pH 4.

Each of the constitutents of the complex can be recovered by destroying it in a NaCl/HCl medium. There is then obtained a precipitate constituted by the urokinase, whilst the heparin passes into solution.

Urokinase heparinate is obtained in the dry state, especially by lyophilisation of these solutions. It is stable and can be preserved as is without difficulty.

Furthermore urokinase heparinate, preserves integrally all its properties, especially the pharmacological and therapeutic properties of urokinase, and gives rise to stabilised solutions in the usual perfusion media, such as 5% serum glucose solutions.

Additional characteristics of the invention will become apparent also in the course of the description of the Examples which follow. It is understood that in the following, all the operations are carried out at a temperature of the order of 4° C, except in the case where a different temperature is expressly stipulated.

EXAMPLE 1

Preparation of purified urokinase

An advantageous operational procedure for obtaining purified urokinase is as follows:

treatment of human urine brought to a pH 5.6 with acetic acid with a filtering additive such as the commercially available under the trademark "hyflosupercel";

extraction at 4° C of the urokinase absorbed on the hyflosupercel, by treating the filtering additive with a 0.32 M solution of disodium phosphate buffer at pH 7.2 and of 2.2 M sodium chloride and separation by filtration of the hyflosupercel; the latter is washed with an eequal volume of buffer solution;

the solutions (filtrate and washings) are combined, brought to a pH 6.25 with 0.5 N phosphoric acid; if necessary the possible viral contaminations are eliminated, particularly by heating to 60° C for 10 hours; it is briskly cooled to 4° C and allowed to stand for 16 hours; the precipitate formed is removed by centrifugation;

to the supernatent liquid, previously brought to a pH 4.2 with 5 N hydrochloric acid, there is added ammonium sulphate to reach 2/3 of saturation in this salt, keeping the temperature between 5° and 8° C;

the precipitate formed, which contains the urokinase, is collected, it is dissolved in two parts of glucose water in the proportion of 18 grams of glucose per liter and the solution is subjected to dialysis until a resistivity of 40,000 microhms is reached; the insolubles are separated by centrifugation and the supernatent liquid is dialysed until a dialysate of resistivity equal to 22,000 microhms is obtained;

treatment of the dialysate with DEAE cellulose (diethylaminoethylcellulose) at a pH 4.5 in the proportion of 25 g for 14,000,000 CTA units of urokinase; it is shaken for 30 minutes, filtered and the resin washed with a solution of ammonium sulphate of resistivity of 15,000 microhms and pH 4.5;

DEAE cellulose at pH 7 is added to the eluate and to the washings, in the proportion of 65 g per 14,000,000 CTA units of urokinase at 2°–4° C, adjusting the pH to 6.6 – 6.8; it is shaken for 30 minutes, water is added to bring the resistivity to 9,000 microhms, the pH is adjusted to 7 and the liquid is filtered, the resin is then washed with a solution of ammonium sulphate or resistivity of 9,000 microhms at pH 7;

after having been brought to pH 6.2, the solution is shaken for an hour at 4° C in contact with kaolin (which has been obtained by placing in suspension kaolin washed in three times its volume of distilled water, this suspension having been brought in the autoclave to 120° C for 90 minutes, then decanted and the kaolin separated and dried in the oven at 200° C);

after centrifugation in the cold, the kaolin is separated and suspended in a solution of a 0.05 M, pH 6.2 phosphate buffer; it is shaken for 30 minutes and the kaolin is separated by centrifugation; the latter washing operation can be repeated several times;

the kaolin is placed in suspension in a solution containing 75 g of ammonium chloride per liter of 4 p. 100 ammonia, and shaken for 30 minutes. The kaolin, separated from the supernatent liquid by centrifugation is subjected to the same elution operation twice in addition;

the supernatent liquids are combined and N/10 $H_2SO_4$ added to obtain a pH of 3.5 and a solution with 350 grammes per liter of ammonium sulphate;

the precipitate collected by centrifugation in the cold is placed in suspension and dialysed against a 0.05 M phosphate buffer solution at pH 6.2 for 18 hours at + 4°;

this dialysed solution is filtered on a column of resin known commercially under the connotation IRC 50, of 5 cm diameter and 60 cm height, equilibrated with the 0.05 M phosphate buffer at pH 6.2; the column is washed with the same buffer until there is no longer a precipitate with 5% trichloacetic acid;

the column of IRC 50 is elluted with an 0.2 M phosphate buffer solution at pH 8.2 in which is dissolved 75 g per liter of ammonium chloride; the eluate is collected in a fraction collector placed in an enclosure at + 4° C;

the fractions containing the activity are precipitated by the ammonium sulphate (350 g/liter) at pH 3.5. The precipitate collected by centrifugation is redissolved at pH 7, diluted sufficiently to obtain a resistivity of the order of 20,000 microhms.

the solution of urokinase thus obtained can again be further purified by means of dialysis under the usual conditions to obtain finally a purified urokinase which can be lyophilised.

EXAMPLE II

Preparation of purified urokinase

One thousand liters of urokinase are collected on phenol. The amount of phenol utilised for this purpose is such that at the end of the collection, the concentration of phenol is at a minimum 0.5%. By the addition of acetic acid, the pH of the urine thus collected is adjusted to 5.8.

Absorption of the urokinase contained in the urine on hyflosupercel

To the mixture is added 5 kg of hyflosupercel and, in a double walled Grignard vessel cooled to 4° C, it is subjected to agitation for 3 hours. The hyflosupercel powder is collected by filtration on a filter press and 17 kg of a paste contained in 12 kg of water is obtained.

Extraction of the urokinase absorbed on the hyflosupercel

To the paste obtained is added 960 g of crystalline sodium chloride and 17 liters of a solution buffered to pH 7.2 obtained by adding into 1,000 ml of demineralised water, 10.8 g of disodium phosphate and 80 g of NaCl. The resistivity of the buffer solution is 84,000 microhms at 15° C.

After 30 minutes shaking, the hyflosupercel powder is separated from the mixture by filtration on a 200 mm diameter Buckner funnel, lined with a cloth for example of synthetic fibre, such as that marketed under the trademark "Tergal." The powder is allowed to deposit and the filtration is terminated by operating under a suction of 500mm of mercury. Before the powder is completely dry, it is washed with 10 liters of the washing liquid, there is obtained a volume of 30 liters. The urokinase activity of the solution thus obtained is 4 million CTA units.

Precipitation of the urokinase contained in the buffer solution

The pH of the solution is adjusted to 4.2 by the addition of 5 N hydrochloric acid. 13.5 kg of ammonium sulphate added (450 g per liter of solution) and it is agitated until complete solution of the salt.

The mixture is allowed to stand for 12 hours. The precipitate which is formed is collected by centrifugation. For this purpose there is used a commercial centrifuge marketed under the name Alfa Laval of type B 1424 F. There are obtained 60 g of moist precipitate, there is added to the precipitate 60 ml of an aqueuse solution containing 18 g of glucose per liter of water.

The mixture is then dialysed until the final conductivity of the solution containing the urokinase is 22,000 microhms.

It is activated by shaking. The dialysed solution is clarified by centrifugation. The activity of the solution obtained is 4,000,000 CTA units of urokinase.

Exclusion of the urokinase on DEAE cellulose a. 7.1 g of DEAE cellulose is added to the preceding clarified solution and the pH is brought to 4.5. After 30 minutes of agitation, the DEAE cellulose is separated by filtration on a 150 mm diameter Buchner funnel, by operating under a moderate vacuum to prevent the formation of froth.

The DEAE cellulose is washed in two stages with a solution of ammonium sulphate at a conductivity of 15,000 micromhos, at pH 4.5. The volume used for each washing is equal to that of the DEAE cellulose and represents about 250 ml.

During the filtration of the washing solution the flask is kept under vacuum in an ice bath.

The activity of the filtrate is 4,000,000 CTA units.

b. To the filtrate obtained, pH 4.5, is added 17.2 g of DEAE cellulose brought to pH 6.7.

The conductivity is lowered by dilution with water to 9,000 micromhos. After 30 minutes of agitation, the DEAE cellulose is separated by filtration on a porcelain Buchner funnel of 150 mm diameter. Progressively with the filtration the pH of the filtrates or effluents collected is brought to 5 by the addition of 5 N sulfuric acid.

The DEAE cellulose is washed with a solution of ammonium sulphate, of 9,000 micromhos conductivity, at pH 7, until a colourless filtrate is obtained.

The filtrates and washing solutions are combined and adjusted to pH 5. The urokinase activity of the solution obtained is 4,400,000 CTA units.

Absorption of the urokinase on kaolin and separation by elution.

Kaolin is prepared as follows:

1 kg of kaolin is washed and placed in suspension in 3 liters of distilled water. The mixture is left for 90 minutes at 120° C in the autoclave.

After having allowed the material in suspension to settle, the kaolin is separated then placed to dry in the oven at 200° C.

The solution obtained in the course of the last step titrating 4,400,000 CTA units is brought to a pH of 6.8, then after the addition of 65 g of kaolin prepared in the above-indicated manner, to a pH of 6.2. The mixture is subjected to agitation for one hour. The kaolin is then separated by centrifugation in the cold and placed in suspension in a liter of 0.05 M phosphate solution buffered to pH 6.2.

After 30 minutes of shaking, the kaolin is separated by centrifugation.

The 65 g of kaolin are placed in suspension in 500 ml of a solution containing 75 g of ammonium chloride per liter of 4% ammonia, and agitated for 30 minutes. The kaolin, separated from the supernatant liquid by centrifugation, is subjected to the same elution operation twice additionally.

The supernatent liquids obtained on the centrifugations are combined and 0.1 N sulphuric acid added to obtain a pH of 3.5.

By combining the supernatant liquids obtained on the centrifugation, 1,400 ml of eluate are obtained. The pH of the eluate is brought to 3.5 by the addition of 0.1 N sulphuric acid. There is then added 490 g of ammonium sulphate (350 g per liter of eluate). The precipitate formed by centrifugation in the cold is collected and it is placed in suspension in water. There is then carried out for 18 hours a dialysis against a 0.05 M phosphate solution buffered to pH 6.2.

The urokinase activity of the solution obtained is 2,800,000 CTA units.

Filtration of the dialysate on a column of resin

The dialysed solution is filtered on a column of resin of the Amberlite IRC 50 type, 4 cm in diameter and 60 cm in height, previously equilibrated with 0.05 M phosphate solution buffered to pH 6.2.

When the eluate is run from the column, the resin is washed with the buffer solution until the addition of 5% trichloracetic acid no longer causes the formation of a precipitate in the fractions collected.

To elute the urokinase, there is used a buffer solution of 0.2 M phosphate, of pH 8.2, containing 75 g of ammonium chloride per liter of solution. The eluate is collected in a fraction collector. The tubes containing the activity are precipitated by the ammonium sulphate at pH 3.5 to precipitate the urokinase present, in the proportion of 350 g of ammonium sulphate per liter of elluate, namely 158 g for the 450 ml of eluate obtained.

EXAMPLE III

Preparation of purified urokinase

A precipitate in ammonium sulphate containing crude urokinase and obtained under the conditions indicated in paragraph 4 of example II, is treated as follows, starting with a solution itself obtained from human urine, to which the prior concentration method according to paragraphs 1 to 3 of the same example II, has been applied.

A. Conditions of the first exclusion

The precipitate in ammonium sulphate is solubilised in one to two parts of glucose water, in the proportion of 18 grammes of glucose per liter and the pH is adjusted to a value comprised between 4 and 6 and preferably equal to 4.5.

The solution obtained is dialysed against distilled water until there is obtained a conductivity comprised between 30,000 micromhos and 50,000 micromhos, preferably equal to 40,000 micromhos.

The solution obtained is centrifuged to 3,000 g to eliminate the insolubles formed constituted by the non-proteinic impurities.

A further dialysis of the supernatent liquid is carried out until a dialysate is obtained whose conductivity is comprised between 15,000 and 25,000 micromhos, preferably equal to 22,000 micromhos.

DEAE celluloseis added to the solution obtained in the porportion of 25 g of dry resin or 100 g of drained resin previously equilibrated with an 0.11 M ammonium sulphate solution at pH 4.5 (conductivity of 15,000 micromhos at 4° C), by 14 million CTA units of urokinase.

The medium is shaken for a duration of 20 to 40 minutes, preferably 30 minutes.

The resin is drained, especially on a Buchner under slight suction and it is washed with a solution of 0.11 M ammonium sulphate at pH 4.5 until a colourless effluent or filtrate is obtained.

The filtrate and the washing liquids are combined. The total urokinase activity of the solution obtained is substantially equal to that which was used at the start.

B. Conditions of the second exclusion

The above solution is brought to a pH comprised between 6 and 7, preferably of the order of 6.6.

To this solution 60 g of DEAE cellulose powder or 250 g of the drained DEAE cellulose is added, previously equilibrated with an 0.068 M ammonium sulphate solution to pH 7 (conductivity 9,000 micromhos at 4° C), by 14 million CTA units of urokinase. The conductivity of the medium is then 15,000 to 18,000 micromhos.

The conductivity of the medium is then brought to 9,000 micromhos by successive additions of apyrogenic distilled water, so that each addition produces a drop in conductivity of the medium of 1,000 micromhos, each addition being separated by an agitation for a duration of 5 to 15 minutes, preferably equal to 10 minutes.

The pH of the medium is then adjusted to 7 by the addition of 2 M soda. After agitation for a duration of 30 minutes, it is filtered, especially on the stainless Buchner under slight suction, the receiver vessel being kept in a melting ice bath, the resin is washed with a solution of ammonium sulphate of 9,000 micromhos conductivity, 0.068 M and the pH 7 until a colourless filtrate is obtained.

The solution obtained by combining the filtrate and the washing liquids can then be subjected to additional purification treatments, especially by the treatments of absorption on kaolin and of absorption chromatography on resin of the Amberlite type under the conditions described in the principal patent or again by absorption chromatography on carboxymethylcellulose under the following conditions:

C. Absorption chromatography on carboxymethylcellulose

To the above solution, brought to pH 5, is added carboxymethylcellulose in a proportion of 80 g of dry resin per 14 million CTA units of urokinase, the carboxymethylcellulose having previously been equilibrated with a 0.068 M ammonium sulphate solution, 9,000 $\mu$Mhos, at pH 5°–4° C. The suspension is kept moderately shaken for a duration of 12 to 14 hours at a temperature comprised between 2° and 4° C, its pH being kept at 5±0.1.

The suspension is then filtered on crimped paper by means of a procelain Buchner under slight suction. The effluents preserve the initial colouration.

The carboxymethylcellulose is then washed with a solution of ammonium sulphate of 9,000 micromhos at pH 5, until a colourless solution is obtained.

The carboxymethylcellulose is then drained. There is then added an equal volume of a solution of ammonium sulphate 22,000 $\mu$mhos, pH 5 at 4° C.

The temperature being kept at 4° C, the suspension is agitated for 30 minutes, the carboxymethylcellulose being then drained on crimped paper (on a Buchner) and washed with a solution of ammonium sulphate at 22,000 micromhos until a clear solution which does not precipitate with tannin is obtained.

The eluate and the washing liquids are combined to form a solution of purified urokinase containing 80 to 90% of the urokinase activity of the solution resulting from the combination of the effluent and of the washing solutions obtained at the end of the above-said second exclusion chromatography.

The urokinase contained in this solution is precipitated with sodium chloride. This latter precipitation is done by means of strictly pure crystalline sodium chloride in the proportion of 330 g per liter in a solution whose pH has previously been adjusted to a value comprised between 4 and 5.5. After the standing of the medium for an hour at a temperature of 4 to 6° C, a centrifugation at 9,000 g is effected. The supernatent liquid is separated and a precipitate dissolved in a solution containing at least 30 g per liter of sodium chloride, of 28,000 micromhos conductivity at pH 6.8, the concentration of sodium chloride of the above-said solution having to be such that the solution finally obtained has a urokinase activity equal to 200,000 CTA units/ml. The solution obtained is filtered and, after measuring it is frozen in plasma flasks of 250 ml.

EXAMPLE IV

Preparation of purified urokinase

In the following there is described an example of the extraction of urokinase on the larger scale, from 8,700 liters of male human urine.

Treatment of this human urine is effected by the filtration adjuvant of example 1, the urokinase absorbed on the filtration adjuvant is re-extracted and the eluate and the washing liquid from the filtration adjuvant are treated under the conditions indicated in example 1, to obtain 500 g of a precipitate of ammonium sulphate retaining almost all the urokinase activity contained in the volume of urine treated, namely a total of 35 million CTA units.

These 500 g of precipitate are solubilised in a solution of 18 g of glucose of Codex purity in 500 ml of apyrogenic distilled water. It is agitated for 15 minutes at a temperature of 4° C. The pH is then adjusted to the value 4.5 with 2N sulphuric acid. The conductivity of the solution obtained is 90,000 micromhos. The solution is distributed in dialysis tubes, in a proportion of 150 ml per tube. The dialysis is carried out in a cold chamber with slight shaking, against apyrogenic distilled water, at 4° C, until a conductivity equal to 40,000 micromhos in the dialysate is obtained. The latter is then centrifuged in a cooled centrifuge at 3,000 g. The 35 g of insoluble product obtained are separated.

The supernatant liquid is then again subjected to successive dialysis against distilled apyrogenic water, the temperature being kept at 4° C until the obtaining of a conductivity equal to 22,000 micromhos in dialysate especially:

a first dialysis against 5 liters of distilled water for 3 hours, a second dialysis against 5 liters of distilled water for 3 hours, and a third dialysis against 3 liters of distilled water for 2 hours.

The volume of the dialysate obtained is 1,700 ml. Its conductivity at 4° C is 22,000 micromhos.

Its total content of proteins is 27,200 mg, namely 16 mg of proteins per ml of the dialysate.

Its urokinase activity is 30,600,000 CTA units, namely 80,000 CTA units per ml.

The specific urokinase activity per milligram of proteins is 1,125 CTA units.

This dialysate is subjected to the above-said first exclusion chromatography in contact with 218 g of drained DEAE cellulose equivalent to 54.5 g of DEAE cellulose powder of quality 0.9 meq/g. The addition of the DEAE cellulose is effected with shaking, over a period of 30 minutes, the temperature being kept at 4° C. There then follows the separation of the filtrate on the Buchner funnel, under the action of a sufficiently slight suction to avoid the formation of foam. The resin is washed twice on the Buchner funnel each time with 250 ml of a solution of ammonium sulphate of 15,000 micromhos at pH 4.5.

The solution obtained by the combination of the filtrate and of the washing liquids in total 2,280 ml of solution having a conductivity of 18,000 micromhos, is subjected to the second exclusion chromatography on DEAE cellulose at pH 7 under the following conditions:

The pH of the preceding solution kept at 4° C is adjusted to the value 6.6 by 2 N soda. There is added to this solution 528 g of drained DEAE cellulose, that is to say the equivalent of 132 g of DEAE cellulose powder of a quality 0.9 meq/g. The medium, kept at 4° C, is shaken for 30 minutes.

The mixture obtained at pH 6.6 has a conductivity of 16,000 micromhos.

A first addition at 4° C of 400 ml of apyrogenic distilled water is made and the mixture is shaken for 10 minutes. The conductivity of the mixture at the end of this shaking is 15,000 micromhos.

A second addition of 400 ml of apyrogenic distilled water is then made and gain the medium is shaken for 10 minutes. The conductivity of the mixture at the end of this shaking is 40,000 micromhos.

A third and then a fourth then a fifth and then a sixth dilution are made under the same conditions, the conductivity of the mixture at the end of the sixth dilution being 9,000 micromhos.

The pH of the medium is then adjusted to 7 by 2 N soda and the shaking is maintained for 30 minutes.

Separation of the resin by filtration on the Buchner funnel under a slight suction then follows. The resin is washed with a solution of ammonium sulphate at 9,000 micromhos at pH 7 until a colourless filtrate is obtained.

A volume of solution of 6,000 ml after combination of the filtrate and of the washing liquids (1,500 ml) is then obtained.

Titrations carried out on this solution lead to the following results:

Total content of proteins: 14,400 mg, namely 2.4 mg per ml;

Total acitvity of urokinase: 34,800,000 CTA units, namely 5,800 CTA units per ml;

Specific urokinase activity per mg of proteins: 2,400 CTA units.

The solution obtained can then undergo additional purification according to any one of the known techniques for this purpose, especially those which have been considered in example I or in the principal French patent application at the corresponding stage.

In the preceding example particularly favourable results were obtained. The value of the ratio of the amount of resin used in the second exclusion chromatography to the urokinase activity of the solution to be treated was equal to 43.5 grams of resin per 10 million CTA units of urokinase activity. This value was comprised within the most favourable range, as is shown by the results of a series of tests which have been carried out on the same solution, at the stage of the second exclusion chromatography, with variable amounts of resin, all the other perameters having been otherwise identical.

The results, which have enabled the determination of the range of proportions most favourable under the conditions of practice, are expressed in the following by the amount of resin (denoted by the abbreviation DEAE) expressed in grams and related to 10 million CTA units of urokinase activity:

25 g of DEAE: all the proteins pass into the effluent with the urokinase. 30 g of DEAE: 40 g of DEAE: lower limit giving satisfactory results, the specific activity (acitivity of urokinase relative to weight of proteins) increases, and the urokinase passes wholly into the effluent. 43.5 g of DEAE: 48 g of DEAE: D° upper limit. 53 g of DEAE: the specific activiy does not increase further and loss commences of a certain amount of urokinase acitivity which is absorbed on the resin. 60 g of DEAE: the preceding phenomenon is accentuated.

It will be observed that similar results are obtained for values of the conductivities of the solution subjected to the second exclusion chromatography, other than 22,000 micromhos, but of course comprised within the above-indicated range.

As a result of which there is obtained a particularly effective method of preparing purified urokinases with yields which have never been achieved hitherto, and, simultaneously, and extremely high increase in its specific activity relative to the weight of proteins accompanying it in the motor urine.

EXAMPLE V

Preparation of apyrogenic urokinase

The final precipitate of example II is collected by centifugation and dissolved in apyrogenic and sterile distilled water, so as to obtain the conductivity comprised between 15,000 and 25,000 micromhos. The concentration of this solution of proteins is of the order of 2 mg/ml.

The pH being adjusted to the value of 3.8 and the temperature comprised between 0° and 4° C, there is added to this medium a saturated solution of ammonium sulphate until a saturaton of 0.3 is obtained (namely a solution of 1.22 M ammonium sulphate). The medium is shaken for 15 minutes, then left to stand, also for 15 minutes.

The precipitate is collected by contrifugation at 10,000 g (fraction A).

To the supernatuent liquid is added pure ammonium sulphate, in a proportion of 250 g/l, at pH 3–3.5, then shaken for 30 minutes. The precipitate containing the urokinase is collected by centrifugation at 10,000 g (fraction B).

Results

Each of these precipitates (fractions A and B) is restored to suspension in apyrogenic and sterile distilled water, the pH of the suspension being brought to 7, the suspension then being finally filtered on a 0.22 $\mu$ membrane in a sterile medium.

The filtrate coming from fraction A contains about 5% of urokinase activity.

The filtrate coming from fraction B contains about 95% of urokinase activity of the initial solution.

The fraction A shows itself in practice to retain the whole of the pyrogenic substances initially contained in the initial solution obtained by dissolving the precipitate in ammonium sulphate before fractionation. The fraction B is on the other hand free of pyrogenic substances according to French Pharmacopea standards, loc-cit. These results will be evident from table 1 below in which there are reported the increases in temperature observed respectively in separate series of three rabbits for each of the fractions tested, and in an additional series of eight rabbits for fraction B, all these rabbits having received the doses indicated in the left hand portion of the table, under the conditions provided by the French Pharmacopea.

TABLE I

| Solutions or fractions tested | Increase in temperature in ° C | | | |
|---|---|---|---|---|
| | Series of 3 rabbits | Series of 8 rabbits | Average Value (3 rabbits) | Average Value (8 rabbits) |
| Initial Solution: 3,000 uCTA/kg | 0°5 0°8 0°9 | | 0°7 | |
| Fraction A 3,000 uCTA/kg | 0°9 0°9 1° | | 0°9 | |
| Fraction B 15,00 uCTA/kg | 0°1 0°2 0° | 0°, 0°, 0°, 0°, 0°1, 0°3, 0°4, 0°1 | 0°1 | 0°1 |

EXAMPLE VI

Preparation apyrogenic urokinase

A. Preparation of a purified and concentrated urokinase solution

The procedure starts with 22,000 liters of human urine and there follows extraction of the crude urokinase under the conditions indentical with those of example III above, except as regards the absorption chromatography step on carboxymethylcellulose, on the solution obtained on the emerging from the step of the second exclusion in contact with DEAE cellulose resin, this absorption chromatography being effected as follows:

The above-said solution, brought to pH 5, is treated with carboxymethylcellulose in the proportion of 80 g of dry resin per 14,000 CTA units of urokinase, the carboxymethylcellulose having previously been equilibrated with a solution of ammonium sulphate at 9,000 uMhos, pH 5, = 0.068 M. The suspension is kept moderately shaken for a duration of 12 to 14 hours at a temperature comprised between 2° and 4° C, its pH being kept at 5 ± 0.1.

The suspension is then filtered on crimped paper through a porcelain Buchner funnel under slight suction. The effluents conserve the initial colour.

The carboxymethylcellulose is then washed with a solution of ammonium sulphate of 9,000 micromhos at pH 5, then by a phosphate buffer 0.05 M at pH 6.5, for the purpose of removing the sulphates, until a colourless solution is obtained.

The carboxymethylcellulose is then drained. There is then added to the latter a volume of 0.5 M phosphate buffer equal to the weight of the 0.05 M buffer retained in the drained carboxymethylcellulose at a temperature of 15° –20° C with shaking. There is next added an equal volume of an 0.29 M sodium phosphate. buffer, then a 0.5 M phosphate buffer, to obtain a final molarity of 0.29 M at a pH of the order 6.8 to 6.9.

The temperature is then brought to 6° C, the suspension is shaken for 30 mintues, the carboxymethylcellulose being then drained on crimped paper (on the Buchner funnel) and washed with an 0.29 M phosphate buffer until a clear solution is obtained which does not precipitate withe tannin.

The elluate and the washing liquids are combined to form a purified solution of urokinase containing 80 to 90% of the urokinase activity of the solution resulting from the combination of he effluent and the washing solutions obtained at the end of the second above-said exclusion chromatography.

B. Depyrogenation

The purified solution obtained, which contains 65,000,000 CTA of urokinase is brought to pH 3.5 and the urokinase is precipitated by ammonium sulphate, in the proportion of 350 g of ammonium sulphate per liter of eluate. There is obtained 35 g of a precipitate titrating a total of 65,000,000 CTA units of urokinase.

This precipate is dissolved in 600 ml of sterile apyrogenic distilled water, the solution obtained having, at pH 3.8, a conductivity of 15,000 micromhos and a content of proteins of 2 mg/ml.

This solution causes in the pyrogenic test on the rabbit a hyperthermia of $0.9°$ C at the does of 3,000 CTA units/kg.

There is slowly added with stirring 258 ml of a saturated solution of ammonium sulphate previously brought to pH 4 and at $4°$ C. The pH of the medium is brought to pH 3.8, shaken for 15 minutes, then allowed to stand for 15 minutes.

The slight precipitate formed is collected by centrifugation at 10,000 g: 5g of precipitate are isolated (fraction C).

The supernatent liquid is treated with pure crystalline ammonium sulphate, in the proportion of 250 g/liter, stirred for 30 munutes. The pH of the medium is then brought to 3 by the addition of several drops of 2 N sulphuric acid. The precipitate formed is collected by centrifugation at 10,000 g and the supernatent liquid is separated: there are obtained 25 g of precipitate (fraction D).

C. Results

The precipitate of fraction C is dissolved in 25 ml of sterile apyrogenic distilled water, and the pH is brought to 7 by 0.1 N soda. The solution obtained is filtered under sterile conditions:

Its titre in urokinase is equal to 10,000 CTA units/ml. The precipitate of fraction D is dissolved in 150 ml of sterile apyrogenic distilled water. The pH is brought to 7 by 0.1 N soda and the solution obtained in filtered under sterile conditions.

Its titre in urokinase is equal to 300,000 CTA units/ml.

Its specific activity to protein is 43,000 CTA units per mg of proteins.

The same observations can be drawn as in the previous case. It is observed that the major portion of the pyrogenic substances has been retained in fraction C, whilst fraction D is free of pyrogenic substances according to the French Pharmacopea standards, as will be apparent from table II below established under similar conditions to those relating with respect to table I.

It is sel-evident that instead of ammonium sulphate there may be used any other salt known for its aptitude to precipitate proteins, such as, for example, magnesium sulphate, sodium chloride, etc, it being understood that it is necessary in each case, to determine previously the degree of saturation of the initial solution of the salt concerned which would lead to a precipitation of proteins under the above-indicated conditions.

TABLE II

| Solutions or fractions tested | Increase in temperature in each of the tested rabbits | | | |
|---|---|---|---|---|
| | Series of 3 rabbits | Series of 8 rabbits | Average Value (3 rabbits) | Average Value (8 rabbits) |
| Initial solution 3,000 uCTA/kg | $1°1$, $0°9$, $0°8$ | | $0°9$ | |
| Fraction C 3,000 uCTA/kg | $0°9$, $0°8$, $0°8$ | | $0°8$ | |
| Fraction D 15,000 uCTA/kg | $0°1$, $0°$, $0°1$ | $0°,0°$, $0°,0°3$, $0°1, 0°1$, $0°3, 0°$ | $0°07$ | $0°1$ |
| Fraction D 20,000 uCTA/kg | | $0°, 0°$, $0°, 0°$, $0°1, 0°1$, $0°3, 0°3$ | | $0°1$ |

As a result of which there is obtained a method of depyrogenation, and also of concentration relative to the urokinase with regard to its protein content, which is simple and particularly effective, with a yield of at least 95% of urokinase activity, the urokinase obtained, apyrogenic at high doses, being then administrable to patients without any secondary effects at doses of 150,000 uCTA or more, in a single injection by the intravenous route, for the treatment of the above-mentioned disorders, others as is, or in another form, for example after conversion into urokinase heparinate, for example under the conditions described below:

EXAMPLE VII

Preparation of urokinase heparinate

Urokinase heparinate can be prepared from a solution of purified and concentrated urokinase by having recourse to the following method of operation.

There is added to this solution, heparine, for example in the proportion of 50,000 units of heparine per 14,000,000 CTA units of urokinase; the pH is brought to 4.2 below 0.5 N phosphoric acids; it is allowed to stand for an hour at the temperature of $4°$ C; it is centrifuged, the mass from the centrifugation is collected with a solution of 10 g/liter of sodium chloride in the proportion of 100 ml of solution per 14,000,000 CTA of urokinase and it is lyophilised to obtain anhydrous urokinase heparinate.

EXAMPLE VIII

Preparation of urokinase heparinate

The initial solution of purified uorkinase has been obtained by the application of the operational method described in example II. Its total urokinase activity if 4,950,000 CTAu.

There is added to this solution 50,000 units of apyrogenic heparine and the pH is brought to 4.2 by the addition of 0.5 N phosphoric acid. The precipitate which is formed is allowed to floculate, for 30 minutes, then it is collected by centrifugation.

The supernatent liquid has an activity less than 25 CTA units/1.

The precipitate is dissolved in 20 ml of a solution of 30 g of sodium chloride per liter, of which the pH is adjusted to 7.3.

The urokinase activity of the solution is 200,000 CTA units/ml, which corresponds to a total of 4,000,000 CTA units.

Urokinase heparinate in the dry state is obtained by proceding with lyophilisation of the solution obtained.

By working in a similar manner, urokinase heparinate may also be prepared from purified urokinases and, if necessary, also depyrogenated, especially from purified fractions of the other examples above.

In the foregoing examples, the reaction of formation of urokinase heparinate was effected at pH 4.2. This value of pH is not critical. However a pH too feebly acid leads to the urokinase heparinate formed solubilising in the reaction medium, which renders its separation more difficult. At too acid a pH, the urokinase would risk undergoing degradation. Good results are obtained within a range of pH of 1 to 5.

It is observed that the proteins which still accompany the urokinase in the purified urokinase preparations are also fixed by the heparine. The relative specific activities of the urokinase and of heparine will hence to a certain degree be a function of the degree of purification of the initial urokinase preparation.

Thus urokinase heparinates can be prepared whose relative activities can be of the order of 30,000 to 100,000 CTAu for 100 I.U. of heparine.

By taking highly purified starting products, namely urokinase at 100,000 CTAu/mg, heparin at 160 Iu/mg, it is noted that 1 mg of urokinase complexes with about 0.6 mg of heparine, The specific activity of such a heparine-urokinase complex is as follows:

| | |
|---|---|
| Expressed as urokinase: | 62,600 CTAu/mg |
| Expressed as heparine : | 100 Iu/mg. |

As indicated below, by way of example, the activities of urokinase, in CTAu/mg (CTA units/mg), and the activities of heparine in international units of heparine/mg (Iu/mg) respectively, of batches of urokinase heparinate obtained by the application of the method according to the invention.

TABLE III

| | Urokinase Activity (CTAu/mg) | Heparine Activity (Iu/mg) |
|---|---|---|
| A | 54,800 | 60.7 |
| B | 32,000 | 27.1 |
| C | 50,500 | 52 |
| D | 62,000 | 72 |
| E | 51,500 | 57 |

In the following there will be described certain of the properties of urokinase heparinate, and, by way of example, certain of its characteristic clinical applications.

A. Stability of urokinase heparinate

Urokinase heparinate is remarkably stable and can be preserved for extended periods. There is indicated in table IV below the results of tests carried out on a batch titrating originally 48,750 CTAu/mg at successive intervals of time (it is to be noted that the accuracy of the test is plus or minus 10%):

TABLE IV

| Time of Test | Urokinase activity in CTAu/mg |
|---|---|
| At the start | 48,750 |
| 3 weeks after | 46,875 |
| 1 month after | 50,000 |
| 10 weeks after | 50,000 |
| 4 months after | 50,000 |
| 5 months after | 50,000 |

These results show that the urokinase heparinate is perfectly stably; which is not the case with non-complexed urokinase, which, in the lyophilised or frozen form, loses 20 to 20% of its acitivity in 24 – 48 hours.

The urokinase heparinate gives rise to stabilised solutions in the usual perfusion media, such as solutions of 5% glucose serum, as emerges from the comparative tests below.

The variations as a function of time of activity are compared, at a temperature of 22° C, of solutions of urokinase heparinate, on one hand, and of heparinate, on the other hand, in 5% glucose serum.

| | Urokinase in the 5% glucose serum: Titres in CTA units | Loss % | Urokinase heparinate in 5% glucose serum: Titres in CTA units | Loss % |
|---|---|---|---|---|
| At the start | 250 | — | 300 | — |
| After 2 h. | 175 | 30 | 250 | 16.6 |
| After 4h30 | 180 | 30 | 250 | 16.6 |
| After 5h30 | 175 | 30 | 250 | 16.6 |
| After 24 h. | 150 | 40 | 250 | 16.6 |
| After 48 h. | 120 | 52 | 250 | 16.6 |

The examination of the results collected in this table establish that the acitivity of urokinase heparinate in a solution conforming to those used for intravenous perfusions is rapidly stablised, whilst similar solutions of urokinase alone gradually become degraded.

B. Pharmacological properties of urokinase heparinate

1. Action on fibrin clots

According to the technique described by E. VAIREL and R. COURBIER in "Role of the arterial wall in the physiology of fibrinolysis" in "Role of the arterial wall in atherogenesis," Edit. CNRS, Paris 1967, part II, P. 561 – 569, an obstruction is induced in twenty dogs, by intra-arterial clotting.

After arteriographic checking, half of these animals were treated with a solution of urokinase heparinate titrating 50,000 CTA units, by intravenous perfusion for 90 minutes, the untreated animals serving as controls.

At the end of the perfusion, a check arteriography was carried out and then arteriotomy of the segment of the artery obstructed was carried out.

There was noted in the treated animals a complete lysis of the clot which obstructed the artery. On the other hand, in the control animals the arteriographic check, and then the arteriotomy, showed the persistance of the arterial obstruction.

2. Pyrogenic substances

Urokinase heparinate obtained from purified and depyrogenated urokinase according to the invention is itself devoid of pyrogenic substances within the standards which have been applied in examples V and VI.

3. Vasopressive substances

Urokinase heparinate, especially that obtained from the above-said depyrogenated urokinases, is devoid of vasopressive substances.

The study was carried by having recourse to an injection of urokinase heparinate in six male dogs of the Beagle breed, aged about 8 months and weighing 9 to 15 kg, at the dose of 20,000 CTAu/kg, these dogs having been anesthetised by an injection of pentothal 1¼ hours before the administration of the urokinase heparinate. The measurements of the arterial pressure were effected continuously for duration of 300 minutes after the injection. They did not reveal changes in the arterial pressure other than those which are observed equally in 4 dogs, when the same dogs are injected with the same dose of pentothal, without the subsequent injection of urokinase heparinate. The complex according to the invention is hence perfectly tolerated.

A study carried out in the rabbit, and involving 4 animals receiving 100,000 CTAu/kg in five injections of 50,000 units every 15 minutes, showed the same tolerence to the product.

4. Thromboplastin

In several animals it was verified, by means of a thrombelastorgram, that the intravenous injection of high doses of heparin -urokinase in the rabbit (100,000 CTAu/kg/hour) only involved a hypocoagulability due to the heparin, without rebound effects after neutralisation of the anticoagulant by protamine sulphate or after its spontaneous elimination.

C. Clinical tests

1. The administration of the urokinase in the state of a complex with heparin is particularly easy, due to its greater stability than that of non-complexed urokinase, in the perfusion media, as is borne out the results of the following clinical trials with preparation of heparinate of urokinase in solution in glucose serum, no patients afflicted with various circulatory disorders leading to the formation of obstructing clots. The heparinate of urokinase is administered by intravenous perfusion, for 24 hours, at the dose of 50,000 to 100,000 CTA units/h.

The observations and results obtained are reported below:

in a patient long afflicted with arteritis and whose aortic fork is constituted by a dacron prothesis, the said treatment enables the obtaining in two administrations, in 8 to 12 hours, of lysis of the clots obstructing the prothesis;

in a patient suffering from retinial thrombosis, treated by perfusion for an hour with a solution of urokinase heparinate titrating 100,000 CTA units, then during the following hours with a solution titrating 50,000 CTA units, it was noted by ophthalmoscopic checking that the lysis of the thrombosis was achieved 8 hours after the beginning of the treatment;

in a patient in a generally precarious condition whose phlebographis examination showed serious phlegmatia alba dolens of the lower member, there was noted by administration of 50,000 CTA units/h of urokinase heparinate, a complete regression of the phlegmatia alba dolens in 18 hours.

Phlebographic examination carried out at the end of 48 hours enables it to be established that the thrombus, which obstructed the deep femoral vein from its popliteal source at its iliac end, underwent lysis.

It emerged from examination of these results that urokinase heparinate constitutes a remarkable thrombolytic agent, leading in a relatively short time to the freeing of an arterial or veinous segment obstructed by clots.

In all the tests which have been described the stability of urokinase heparinate in solution was such that it was not necessary in any of the cases to regenerate the perfusion medium with urokinase, during the whole duration of the perfusion operation.

The advantage of the complex according to the invention is therefore increased by the fact that it is well tolerated by the organism that its use has no repercussion on the coagulation factors of the circulating blood and that it does into cause any hemorrhagic accident or effect.

2. The foregoing results have been obtained with highly purified prepartions of urokinase, but which had not undergone depyrogenation treatment according to the invention.

The following report relates to clinical observations effected with urokinase preparations in the form of purified and also depyrogenated urokinase heparinate. The use of these preparations led to the remarkable results described below, in the absence of any undesirable secondary effect.

a. The administration of urokinase heparinate free of pyrogenic substances to ten patients having syndromes of myocardial infarctus, more or less advanced, at repeated doses of 75,000 to 150,000 CTA units, resulted in all cases in a rapid and favourable development of the syndromes observed from the first days of treatment.

Given below are the main lines of one of these ten clinical observations which are particularly typical relative to the action of urokinase heparinate free of pyrogenic substances.

B. John Louis, 44 years, teacher of handicapped children, was hospitalised for a syndrome of threatened myocardial infarctus. He had sufferred for a week from anginal distress accompanied by hyperthermia. The electrocardiogram showed an extended sub-epicardial ischemia.

He received by perfusion a treatment based on urokinase heparinate at the dose of 75,000 CTA units per hour for 24 hours, namely in all 1,850,000 CTA units, of heparin (30 mg every two hours) and of the corticosteroid marketed under the trademark SOLUDECADRON.

On the clinical level there was observed a regression of the hyperthermia the disappearance of the anginal syndrome from the fourth hour of treatment. Electrocardiography revealed rapid favourable development in the course of the 24 hours of th treatment. At the end of 8 days the electrocardiogram was again practically normal.

On the biological level there was observed in parallel a rapid reduction in plasminoqenic levels, which was manifested by rapid transformation of the latter into plasmin, and a rapid increase in the fibrin degradation products, pointing to lysis of the fibrin of the pathologic clot.

The sequellae which remained in the patient after his convalescence are at this point so reduced that he can resume his work.

b. There are also indicated below the results obtained in the treatment of 15 patients suffering from myocardial infarctus.

Generalities and methods

Study of the therapeutic action of urokinase heparinate in a group of 15 patients was carried out in the following way:

a. Selection of patients:

Infarcuts dating from at least 48 hours.

b. Criteria for estimation of the therapeutic activity

Clinical development:
 disappearance of pain; resumption of physical activity; decease in average time (30 days).
Electrocardiographic development:
 tri-scintigraphic development
Evaluation of the biological activity of the urokinase administered according to the diagram:
 Evaluation of the plasminogenic levels;
 Evaluation of fibrinogenic levels;
 Evaluation of lysis products;
 Evaluation of tolerance:
 arterial pressure
 temperature
 clinical and biological signs which can be attributed to the urokinase, with the exception of those connected with its specific activity.

c. Therapeutic diagram:

Urokinase heparinate: 75,000 CTAu/hour for 24 hours administered by perfusion. The urokinase heparinate is diluted in an isotonic glucose solution. Heparine: Administered by the sub-cutaneous route, with a posology adapted as a function of the condition of the patient to obtain efficient and stable hypocoagulability (Howell time of the patient double that of the control). Results:

a. 15 patients treated:

14 men, 1 woman. Age comprised between 41 and 74 years.

b. Overall clinical developments:

Disappearance of pain between 1 hour and 4 hours after the beginning of treatment, except in one case.

Time of hospitalisation: between 23 and 36 days.

Resumption of passive activity in bed: between 3 and 14 days.

Mobilisation and getting up: between 9 and 23 days.

This group of patients is representative. The time of disappearance of the pain, of mobilisation and of ambulation are shorter than those conventionally observed in a group of myocardial infarctus patients untreated with urokinase.

In this group, no death was observed: in a comparable group of patients — not treated with urokinase - mortality was 26%; it is 18% when another thrombolytic medicament is administered (Streptokinase).

No hemorrhagic accident was observed, the tolerence of urokinase was perfect; there was noted neither modification of the temperature, nor change in arterial pressure, nor any clinical or biological change attributable to this medicament, outside of those strictly connected with its specific activity.

Overall electrocardiographic development 9 cases of ischemia or of ischemia-lesion Electrocardiographic tracing normal or practically normal in 6 cases. Average time: 22 days. Ischemia-lesion condition sequellae in 3 cases (but in 2 cases, there existed a ventricular ectasia pre-existing to the treatment).

6 cases of necrosis and ischemia syndrome

Electrocardiographic tracing in normal or practically normal with complete regression of the necrosis in 3 cases. Average time: 26 days. Considerable regression of the necrosis in 3 cases (in one case, ventricular ectasia was pre-existing). This electrocardiographic development is more rapid than that normally observed in a same group of myocardial infarctus not treated with urokinase.

Scintigraphic development

Each time that the cardiac scintigraph (scintigraph of the myocardia, cavitary scintigraphy and coronary scintigraphy) was carried out — before and after treatment — namely 21 days after the first examination, it was strictly parallel with that of the elctrocardiogram (in particular the scintigraphy was the result of ventricular ectasia pre-existing to the treatment, in the same way as that resulting from the regression or the disappearance of the necrosis as well as the regression or the disappearance of the ischemia syndrome).

Biological evaluation

Plasminogen

Initial levels comprised between 90 and 120%.

Maximum fall observed: between 43 and 11%. The fall is significant.

Fibrinogen

Initial levels comprised between 10.80 g/l and 1.96 g/l.

Minimum levels observed under treatment: between 6.36 g/l and 1.85 g/l. The modifications observed are not significant.

Decradation products of fibrin:

Initial levels comprised between 0.4 $\mu$ and 12.80 $\mu$

Levels ovserved under treatment: between 320 $\mu$ and 2660 $\mu$.

The modifications observed are significant.

Conclusion

In this group of 15 myocardial infarctus treated with urokinase heparinate at the dose of 75,000 CTAu/hour for 24 hours, and by comparison with a comparable group of untreated patients, there were obtained:

in 14 out of 15 cases, rapid regression of pain without resumption of anginal syndromes;

a more precocious resumption of physical activity either passive, or active;

no death, no hemorrhagic accident, the tolerence was perfect;

electrocardiographic development coroborated by scintigraphic development is shorter than that observed in the control group.

As emerges from the foregoing clinical observations, urokinase heparinate hence constitutes a fibrinolytic and thrombolytic medicament of great value, in both man and animal.

Although in the foregoing examples urokinase heparinate was administered by enovenous perfusion, recourse can be had to other types of perfusion, such as perfusions is situ, especially intrapleural.

The posologies had to be adapted to the case of each patient. They indicte in general doses comprised within a range of 50,000 to 150,000, preferably 50,0000 to 100,000 CTAu/hour, for 24 hours.

Urokinase heparinate can be administered in solution in any perfusion medium acceptable to the organism, compatible with the urokinase, not precipitating with heparin and free of mineral salts. A preferred perfusin medium is constituted by isotonic glucose serum.

Urokinase heparinate is stable in these media at all dilutions. For the purposes of administration the dilutions selected will be those which enable administration of the above-indicated doses, without the perfused volumes exceeding the values tolerated by the organism, these volumes having to be however sufficient for a continuous perfusion "drop by drop" to be effected. When the perfusin medium is constituted by isotonic glucose serum, there is advantageously selected a dilution permitting the administration of selected doses of urokinase heparinate at the rate of about 250ml of solution/6 hours, namely dilutions of about 300,000 to 900,000, preferably 300,000 to 600,000 CTAu of urokinase/250 ml.

It must be understood that is using micromhos units as regards the values of the conductivity it is meant micromhos per centimeter. Similarly in expressing the resistivity in microhms it is meant microhms centimeter.

As is self-evident and as emerges already from the foregoing, the invention is in no way limited to those types of application and embodiments which have been more especially considered; it encompasses on the contrary, all modifications.

What we claim is:

1. Solution for perfusion, containing an effective amount urokinase heparinate in association with an isotonic perfusion solution acceptable by the organism, compatible with urokinase, not precipitating with heparin and free of mineral salts.

2. Solution according to claim 1, wherein said solution is constituted by isotonic glucose serum.

3. Solution according to claim 1, wherein its dilution is of the order of 300,000 to 900,000 CTA units of urokinase/250 ml.

4. Solution according to claim 3, wherein its dilution is of the order of 300,00 to 600,000 CTA units of urokinase/250 ml.

5. Method of treating patients having thrombolytic or fibrinolytic disorders, comprising the administration by perfusion to said patients of effective doses of a solution based on urokinase heparinate according to claim 1.

6. Method according to claim 5, comprising administering to said patients doses of 50,000 to 150,000 CTA units of urokinase/hour for 24 hours.

7. Method according to claim 5, comprising administering to said patients doses of 50,000 to 100,000 CTA units of urokinase/hour for 24 hours.

8. An composition for preventing formation of thrombi or for causing the lysis of thrombi which comprises a therapeutically effective amount of a stable urokinaseheparin complex wherein the urokinase is purified, in combination with a pharmaceutically acceptable carrier.

9. The urolinase-heparin complex of claim 8 wherein the heparin is complexed with highly purified urokinase, the complex having retained essentially all its urokinase activity.

10. The composition of claim 9 wherein the urokinaseheparin complex is apyrogenic.

11. The composition of claim 9 wherein the urokinase-heparin complex is free of vasopressive substances.

12. The composition of claim 9 wherein the urokinase-heparin complex is a lyophilized complex.

13. The composition of claim 9 which is a solution.

14. The composition of claim 13 in which the solution is a isotonic perfusion solution.

15. The composition of claim 9 wherein the activity of heparin respective the activity of urokinase is comparatively negligible.

16. The composition of claim 15 wherein the urokinase-heparin complex has a ratio of heparin to urokinase activity of 100 I.U. per milligram of heparin to 30,000 to 100,000 C.T.A. units per milligram of urokinase.

17. The method of treating thrombo-embolic syndromes which comprises treating a patient so afflicted with a therapeutically effective amount of the composition of claim 9.

18. The method of claim 17 which comprises preventing formation of thrombi.

19. The method of claim 17 which comprises causing the lysis of thrombi.

20. The method of claim 17 which comprises treating myocardial infarctus.

* * * * *